(12) United States Patent
Aswatha Narayana et al.

(10) Patent No.: US 12,181,906 B2
(45) Date of Patent: Dec. 31, 2024

(54) KNOBS FOR ENDOSCOPES WITH IMPROVED USABILITY AND ERGONOMICS

(71) Applicant: Boston Scientific Medical Device Limited, Galway (IE)

(72) Inventors: Balaji Aswatha Narayana, Bangalore (IN); Shrikant V. Raut, Mumbai (IN); Aditya Dhanotiya, Indore (IN)

(73) Assignee: Boston Scientific Medical Device Limited, Galway (IE)

( * ) Notice: Subject to any disclaimer, the term of this patent is extended or adjusted under 35 U.S.C. 154(b) by 0 days.

(21) Appl. No.: 17/818,423

(22) Filed: Aug. 9, 2022

(65) Prior Publication Data

US 2022/0378277 A1    Dec. 1, 2022

Related U.S. Application Data

(63) Continuation of application No. 16/814,417, filed on Mar. 10, 2020, now Pat. No. 11,445,895.

(60) Provisional application No. 62/816,458, filed on Mar. 11, 2019.

(51) Int. Cl.
```
A61B 1/005    (2006.01)
A61B 1/00     (2006.01)
G05G 1/01     (2008.04)
G05G 1/08     (2006.01)
```
(52) U.S. Cl.
CPC ........... *G05G 1/08* (2013.01); *A61B 1/00042* (2022.02); *A61B 1/0052* (2013.01); *G05G 1/01* (2013.01)

(58) Field of Classification Search
CPC .............. A61B 1/00042; A61B 1/0052; A61B 1/00066; G05G 1/08; G05G 1/01
See application file for complete search history.

(56) References Cited

U.S. PATENT DOCUMENTS

| | | | |
|---|---|---|---|
| 3,965,529 A | 6/1976 | Hadzimahalis | |
| 4,207,873 A | 6/1980 | Kruy | |
| 5,007,406 A | 4/1991 | Takahashi et al. | |
| 5,496,260 A | 3/1996 | Krauter et al. | |
| 6,673,012 B2 | 1/2004 | Fujii et al. | |
| 6,958,036 B2 | 10/2005 | Seki et al. | |
| 7,494,462 B2 | 2/2009 | Seki et al. | |

(Continued)

FOREIGN PATENT DOCUMENTS

| | | | |
|---|---|---|---|
| JP | S5884101 U | | 6/1983 |
| JP | 2005245545 A | * | 9/2005 |
| JP | 2006000406 A | | 1/2006 |

OTHER PUBLICATIONS

International Search Report and Written Opinion for corresponding PCT/IB2020/052064, mailed Jun. 15, 2020 (18 pages).

*Primary Examiner* — Anh T Nguyen
*Assistant Examiner* — Rynae E Boler
(74) *Attorney, Agent, or Firm* — Bookoff McAndrews PLLC (57) ABSTRACT

The present disclosure relates generally to the field of medical devices. In particular, the present disclosure relates to medical devices and systems with control knobs designed for improved usability and ergonomics. For example, the control knobs of the present disclosure may include surface features for improved gripping, surface features for improved perception of medical device orientation within a patient and/or knobs dimensioned for improved thumb reach and reduced torque.

19 Claims, 9 Drawing Sheets

(56) References Cited

U.S. PATENT DOCUMENTS

| | | |
|---|---|---|
| 8,808,169 B2 | 8/2014 | Macnamara et al. |
| 8,845,521 B2 | 9/2014 | Maruyama |
| 10,117,567 B2 | 11/2018 | Okamoto |
| 2003/0187328 A1* | 10/2003 | Seki .................... A61B 1/0052 600/146 |
| 2008/0119696 A1* | 5/2008 | Moriyama ........... A61B 1/0052 600/146 |
| 2009/0287188 A1* | 11/2009 | Golden ............. A61M 25/0147 604/528 |
| 2013/0012958 A1* | 1/2013 | Marczyk ............ A61B 17/2909 606/130 |
| 2013/0018306 A1* | 1/2013 | Ludwin ............. A61M 25/0136 604/95.04 |
| 2014/0100424 A1 | 4/2014 | Hoshino |
| 2016/0367111 A1* | 12/2016 | Okamoto ................ A61B 1/005 |

* cited by examiner

Position "K"

KNOBS FOR ENDOSCOPES WITH IMPROVED USABILITY AND ERGONOMICS

CROSS-REFERENCE TO RELATED APPLICATION

The present application is a continuation of and claims the benefit of priority under 35 U.S.C. § 120 to U.S. Nonprovisional patent application Ser. No. 16/814,417, filed Mar. 10, 2020, which claims the benefit of priority under 35 U.S.C. § 119 to U.S. Provisional Patent Application 62/816,458, filed Mar. 11, 2019, the entireties of which are incorporated herein by reference.

FIELD

The present disclosure relates generally to the field of medical devices. In particular, the present disclosure relates to medical devices and systems with control knobs designed for improved usability and ergonomics.

BACKGROUND

Conventional endoscope handles generally include two control knobs for manipulating the distal tip of the endoscope in the up/down and left/right directions. The larger of the two control knobs typically controls movement in the up/down directions, while the smaller of the two control knobs typically controls movement in the left/right directions. Most physicians are trained to hold the endoscope handle in their left hand and operate the large and small control knobs with their left thumb, although some physicians hold the endoscope handle in their left hand and operate the large control knob with their left thumb and the small control knob with their right hand. Each control knob typically includes a series of evenly spaced crests and troughs, which the physician engages with their thumb to rotate the control knob. Many physicians have difficulty reaching and rotating one or both control knobs, especially the small control knob and especially physicians with smaller hands. This difficulty tends to be compounded if the physician is required to operate the endoscope in a tortuous position (e.g., within an extremely curved path within the patient anatomy), a non-ideal environment (e.g., within the confined space of a particularly small operating room or the like), and/or with wet gloves, which tend to slip on the smooth surfaces of the crests and troughs. This difficulty tends to be further compounded when the endoscope is being manipulated in a tortuous body passage due to the strain exerted on the control wires connecting the end of the endoscope to the control knobs, which requires the physician to exert additional force/torque on the control knobs. Considering that a physician may perform multiple (e.g., 5-10) medical procedures per day, each of which may last from less than an hour to more than 3 hours, the repetitive thumb movement may contribute to long term discomfort and/or injury to the physician as well as poorer patient outcomes, e.g., due to increased procedure time, decreased procedure efficiency and/or physician error.

It is with these considerations in mind that a variety of advantageous medical outcomes may be realized by the devices and systems of the present disclosure.

SUMMARY

The present disclosure relates to an endoscopic system comprising a control handle operably attached to a proximal end of an endoscope. A first control knob may be rotatably attached to the control handle and configured to move a distal end of the endoscope in a first direction. A series of crests and troughs may define an outer circumference of the first control knob. A second control knob may be rotatably attached to the control handle and configured to move the distal end of the endoscope in a second direction. A series of crests and troughs may define an outer circumference of the second control knob. The first control knob may be disposed between the control handle and the second control knob. An outer dimension of the first control knob may be greater than a corresponding outer dimension of the second control knob. A gripping surface of the outer circumference of the first control knob may have a first width and a gripping surface of the outer circumference of the second control knob may have a second width. The first width may be substantially equal to the second width. The gripping surfaces of the first and second control knobs may include a textured surface feature. The gripping surfaces of the first and second control knobs may be formed of a material separate from the material of the control knobs and, optionally, co-molded to the outer circumference of the first and second control knobs. The first control knob may define a first opening configured to receive a first portion of a post of the control handle, and the second control knob may define a second opening configured to receive a second portion of the post of the control handle. A lever arm length from the center of the first opening to an end of each crest of the first control knob may be substantially equal and a lever arm length from the center of the second opening to an end of each crest of the second control knob may be substantially equal. The lever arm length of each of the series of crests of the first control knob may be approximately 35.0 mm. The lever arm length of each of the series of crests of the second control knob may be approximately 27.0 mm. The first control knob may define a first opening configured to receive a first portion of a post of the control handle, and the second control knob may define a second opening configured to receive a second portion of the post of the control handle. A lever arm length from the center of the first opening to an end of each crest of the series of crests of the first control knob may be substantially equal. A lever arm length from the center of the second opening to an end of a second crest of the series of crests of the second control knob may be greater than a lever arm length from the center of the second opening to an end of a first and third crest of the series of crests of the second control knob. The lever arm length of the second crest of the second control knob may be approximately 31.0 mm and the lever arm length of the first and third crests of the second control knob may be approximately 29.0 mm. The lever arm length of each crest of the series of crests of the first control knob may be approximately 35.0 mm. The second crest of the second control knob may be between the first and third crests of the second control knob. A lever arm length from the center of the second opening to an end of a fourth, fifth and sixth crest of the series of crests of the second control knob may be less than a lever arm length of the first and third crests of the second control knob. The first control knob may define a first opening configured to receive a first portion of a post of the control handle, and the second control knob may define a second opening configured to receive a second portion of the post of the control handle. A lever arm length from the center of the first opening to an end of a second crest of the series of crests of the first control knob may be greater than a lever arm length from the center of the first opening to an end of a first and third crest of the series of crests of the first control knob. A lever arm length from the center of the second opening to an end of a second crest of the series of crests of the second control knob may be greater than a lever arm length from the center of the second opening to an end of a first and third crest of the series of crests of the second control knob. The lever arm length of the second crest of the first control knob may be approximately 39.0 mm and the lever arm length of the first and third crests of the first control knob may be approximately 36.0 mm. The lever arm length of the second crest of the of the second control knob may be approximately 31.0 mm and the lever arm length of the first and third crests of the second control knob may be approximately 29.0 mm. The second crest of the first control knob may be between the first and third crests of the first control knob. A lever arm length from the center of the first opening to an end of a fourth and fifth crest of the series of crests of the first control knob may be less than a lever arm length of the first and third crests of the first control knob. The second crest of the second control knob may be between the first and third crests of the second control knob. A lever arm length from the center of the second opening to an end of a fourth, fifth and sixth crest of the series of crests of the second control knob may be less than a lever arm length of the first and third crests of the second control knob. The first control knob may define a first opening configured to receive a first portion of a post of the control handle, and the second control knob may define a second opening configured to receive a second portion of the post of the control handle. A lever arm length from the center of the first opening to an end of a first and third crest of the series of crests of the first control knob may be greater than a lever arm length from the center of the first opening to an end of a second crest of the series of crests of the first control knob. A lever arm length from the center of the second opening to an end of a first and third crest of the series of crests of the second control knob may be greater than a lever arm length from the center of the second opening to an end of a second crest of the series of crests of the second control knob. The lever arm length of the first and third crests of the first control knob may be approximately 38.0 mm and a lever arm length the second crest of the first control knob may be approximately 35.0 mm. A lever arm length of the first and third crests of the second control knob may be approximately 32.0 mm and a lever arm length the second crest of the second control knob may be approximately 27.0 mm. An outer surface of a first and third crest of the series of crests of the first control knob may be substantially smooth, and an outer surface of a second crest of the series of crests of the first control knob may include an integrated feature. An outer surface of a first and third crest of the series of crests of the second control knob may be substantially smooth, and an outer surface of a second crest of the series of crests of the second control knob may include an integrated feature. The second crest of the first control knob may be between the first and third crests of the first control knob. The second crest of the second control knob may be between the first and third crests of the second control knob.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices and systems with control knobs designed to provide improved ergonomics and usability of an endoscope (e.g., colonoscopes, duodenoscopes, endoscopic ultrasound (EUS) scopes, etc.), it should be appreciated that a variety of medical devices and systems may be modified to include such control knobs, including, for example, stent delivery systems, laparoscopic devices, patient monitoring systems and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Referring to FIGS. 1A-1D, in one embodiment, an endoscopic system 100 of the present disclosure may include a control handle 110 operably attached to a proximal end of an endoscope (not shown). A first control knob 120 (e.g., which may be larger in diameter than a second control knob 140, described below) may be rotatably attached to the control handle 110 and configured to move a distal end of the endoscope in a first direction (e.g., up or down). For example, one or more wires (e.g., control wires) may extend along or through a length of the endoscope such that a proximal end of the wire(s) is attached to the first control knob and a distal end of the wire(s) is attached to a distal end/distal portion of the endoscope. In various embodiments, the first control knob 120 may be rotated in a first direction (e.g., clockwise) to move the distal end of the endoscope in a first direction (e.g., down), and rotated in a second direction (e.g., opposite, e.g., counterclockwise) to move the distal end of the endoscope in a second direction (e.g., up). A series (e.g., plurality, etc.) of troughs 122 and crests 124a-e may extend around (e.g., define) an outer circumference of the first control knob 120.

A second control knob 140 (e.g., which may be smaller in diameter than the first control knob 120) may be rotatably attached to the control handle 110 and configured to move the distal end of the endoscope in a second direction (e.g., left or right). For example, one or more wires (e.g., control wires) may extend along or through a length of the endoscope such that a proximal end of the wire(s) is attached to the second control knob and a distal end of the wire(s) is attached to the distal end/distal portion of the endoscope and rotated in a first direction (e.g., clockwise) to move the distal end of the endoscope in a first direction (e.g., left), and rotated in a second direction (e.g., counterclockwise) to move the distal end of the endoscope in a second direction (e.g., right). A series (e.g., plurality, etc.) of troughs 142 and crests 144a-f may extend around (e.g., define) an outer circumference of the first control knob 120.

In one embodiment, the first control knob 120 may be disposed between the control handle 110 and the second control knob 140, and an outer dimension (e.g., diameter) of the first control knob 120 may be greater than a corresponding outer dimension (e.g., diameter) of the second control knob 140.

In one embodiment, a gripping surface 128 with a first width (e.g., thickness of the knob in the axial direction along the axis of rotation of the knob) may extend around the outer circumference (e.g., across the troughs and crests) of the first control knob 120 and a gripping surface 148 with a second width (e.g., thickness of the knob in the axial direction along the axis of rotation of the knob) may extend around the outer circumference (e.g., across the troughs and crests) of the second control knob 140. The first width and second width may be substantially equal. The gripping surfaces 128, 148 may be configured in any desired manner for contact by the physician to manipulate the control knobs 120, 140. In various embodiments, the gripping surfaces 128, 148 of either or both of the first and second control knobs 120, 140 may be formed from or otherwise include a material different from the material of the knob, such as a non-slip material(s) (e.g., soft or compliant polymers/rubber, etc.) to prevent or minimize the finger/thumb of a physician grasping or otherwise applying pressure to the troughs and crests from slipping. In addition, or alternatively, a variety of textured surface features (e.g., dimples, depressions, projections, etc.) may be attached to or integrally formed within the non-slip material(s) to further improve grip/friction with the finger/thumb of the physician. In various embodiments, either or both of the gripping surfaces 128, 148 may be attached to the outer circumference of the first and second control knobs 120, 140 using a suitable glue, adhesive or resin. Alternatively, either or both of the gripping surfaces 128, 148 may be integrally formed (e.g., co-extruded, co-molded, etc.) with first and second control knobs 120, 140. It will be appreciated that this feature may be used in conjunction with any of the further features described hereinafter. In addition, it will be appreciated that the gripping surfaces 128, 148 may be formed from the same material as that of the control knobs 120, 140, and may be differentiated from the respective control knobs 120, 140 other than by a difference in material. For instance, different textures may be molded into the contact surfaces of the control knobs 120, 140 to form the gripping surfaces 128, 148.

Although the troughs 122, 142 and crests 124a-e, 144a-f are depicted as uniformly or evenly spaced apart around the circumference of the respective first and second control knobs 120, 140, in various embodiments, a distance between any or all of the troughs and crests may vary. In addition, although the first control knob 120 is depicted as including five crests, and the second control knob 140 is depicted as including six crests, in various embodiments the number of crests of each control knob may vary (e.g., fewer than five crests and/or more than six crests).

Figure 1A:
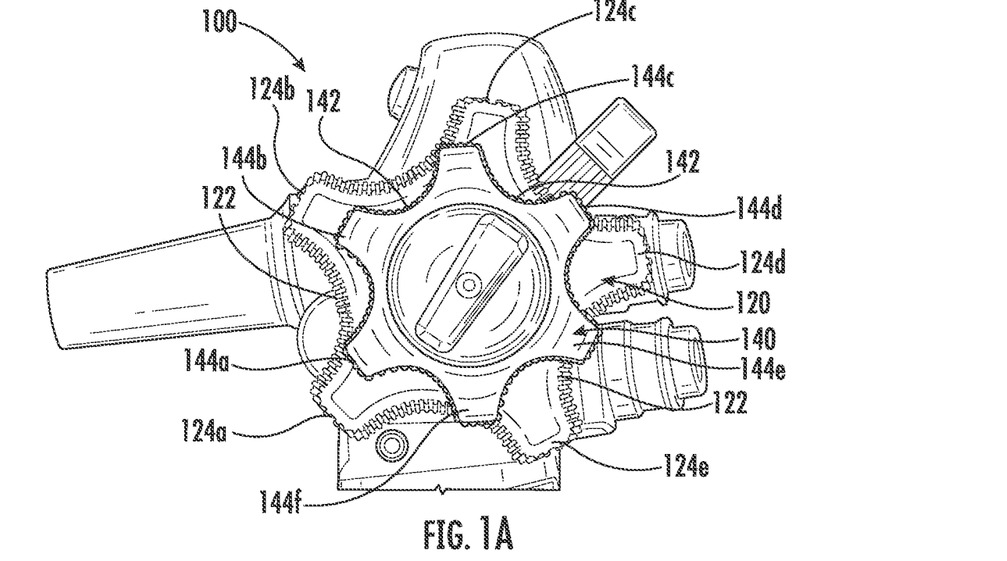
FIGS. 1A-1D and 2A-2C provide perspective views of embodiments of first and second control knobs of an endoscope handle, according to the present disclosure.
Figure 1B:
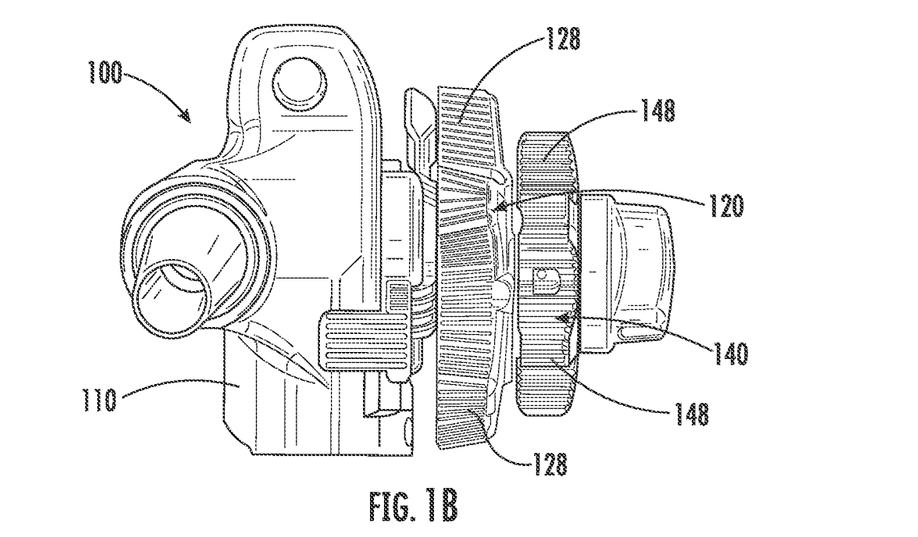
Figure 1C:
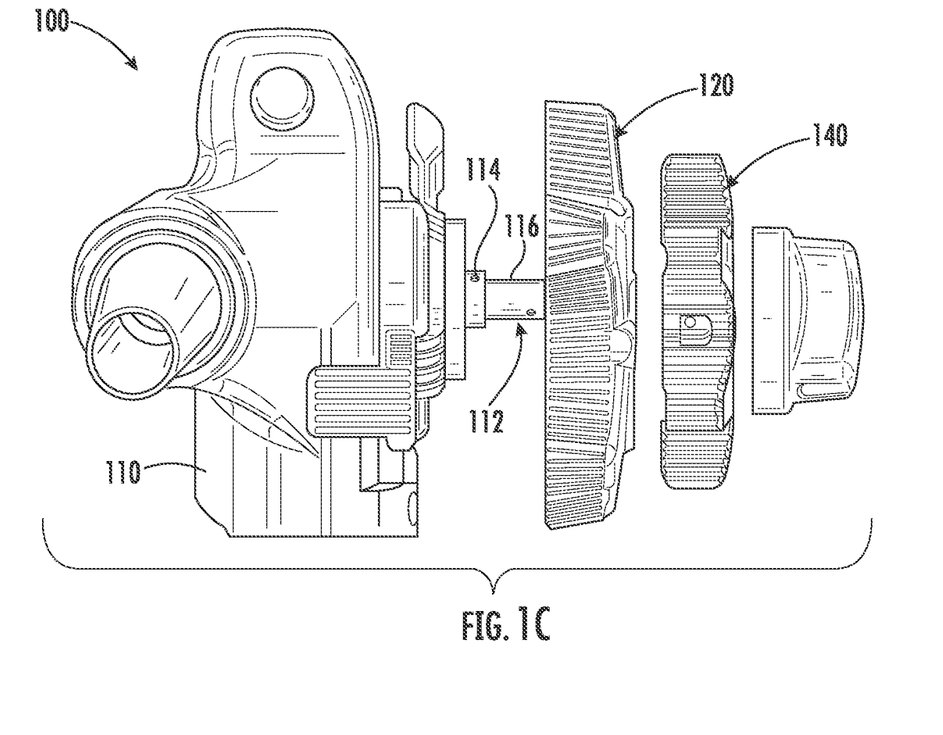
Figure 1D:
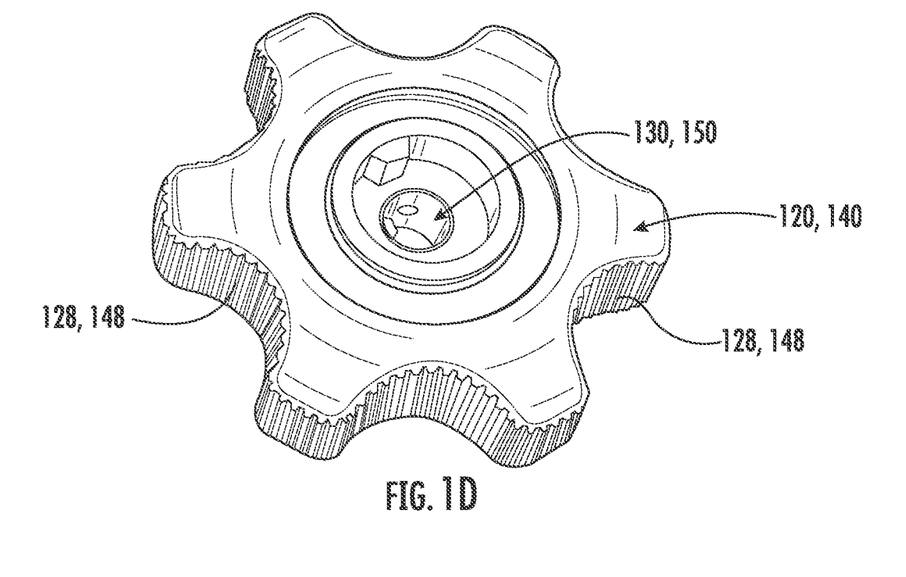

Referring to FIG. 1D, in one embodiment, the first control knob 120 may define a first opening 130 configured to receive a first portion 114 of a post 112 (e.g., mounting shaft; FIG. 1C) of the control handle 110, and the second control knob 140 may define a second opening 150 configured to receive a second portion 116 of the post 112 of the control handle 110. It will be appreciated that the first opening 130 and the second opening 150 may have the same or different diameters.

Figure 2A:
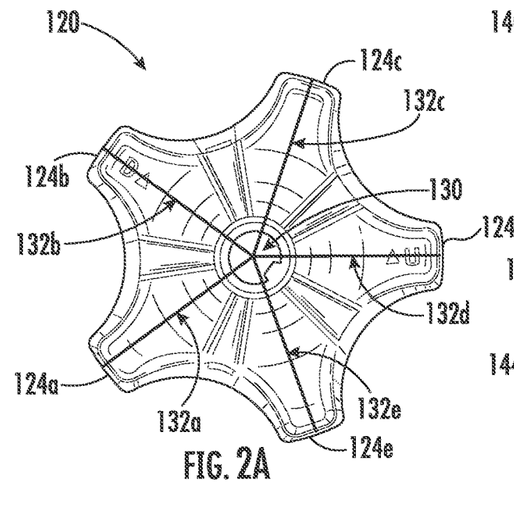
Figure 2B:
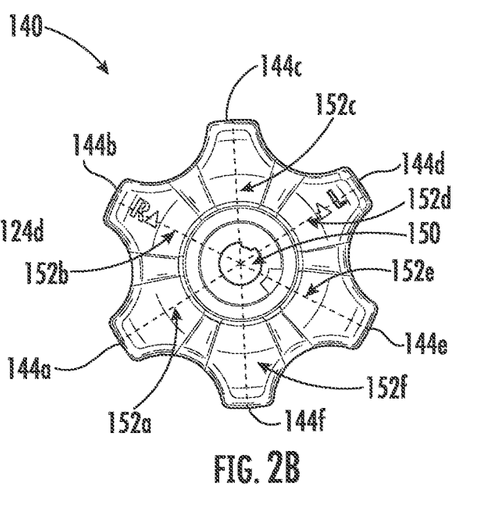
Figure 2C:
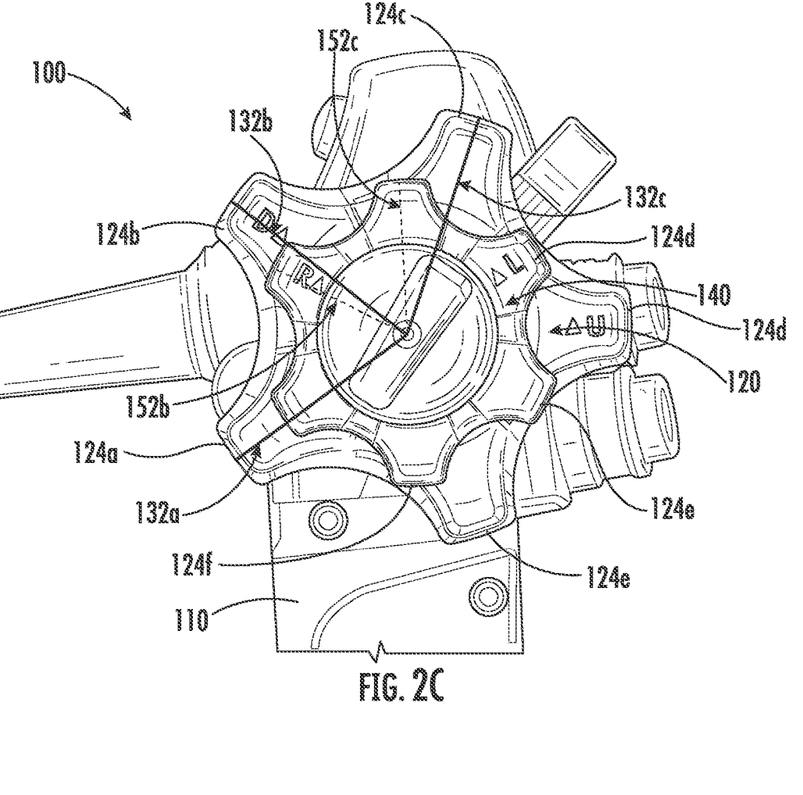

Referring to FIGS. 2A-2C, in one embodiment, the first opening 130 may be substantially centered within (e.g., coaxial, geometrically centered, axis of rotation at a geometric center, etc.) the first control knob 120 such that a lever arm length (e.g., radius) 132a-e from the center of the first opening 130 to an end of each crest 124a-e is substantially equal. For example, the lever arm length 132a-e of each crest 124a-e of the first control knob 120 may be approximately 35.0 mm±2 mm. In addition, the second opening 150 may be substantially centered within (e.g., coaxial, geometrically centered, axis of rotation at a geometric center, etc.) the second control knob 140 such that a lever arm length (e.g., radius) 152a-f from the center of the first opening 150 to an end of each crest 144a-f is substantially equal. For example, the lever arm length 152a-f of each crest 144a-f of the second control knob 140 may be approximately 27.0 mm±2 mm.

Referring to the embodiment of FIGS. 2A-2C, the torque generated on (e.g., force applied to) a crest 124a-e of the first control knob 120 may be determined using the formula $T_B = F_B \times R_B$, where $T_B$ represents torque output, $F_B$ represents the force applied to a crest 124a-e of the first control knob 120, and $R_B$ represents the lever arm length 132a-e of each crest 124a-e. Similarly, the torque generated on (e.g., applied to) a crest 144a-f of the second control knob 140 may be determined using the formula $T_S = F_S \times R_S$, where $T_S$ represents torque output, $F_S$ represents the force applied to a crest 144a-f of the second control knob 140, and $R_S$ represents the lever arm length 152a-f of each crest 144a-f of a given control knob.

Referring to these formulas, with the lever arm lengths 132a-e of the respective crests 124a-e of the first control knob 120 being substantially equal, the torque output ($T_B$) required for the physician to rotate the first control knob 120 may be substantially equal at each crest 124a-e. Similarly, with the lever arm lengths 152a-f of the respective crests 144a-f of the second control knob 140 being substantially equal, the torque output ($T_S$) required for the physician to rotate the second control knob 140 may be substantially equal at each crest 144a-f. Stated differently, none of the crests 124a-e, 144a-f of the first or second control knobs 120, 140 may provide the physician with a mechanical advantage (e.g., reduced torque output $T_B$, $T_S$ to rotate the respective first or second control knobs 120, 140) as compared to another one of the crests 124a-e, 144a-f.

In use and by way of example, a physician may grasp a control handle 110 of an endoscope with their left hand and extend their left thumb to contact the first and second control knobs 120, 140. In various embodiments, the physician may realize several advantages when contacting the gripping surfaces 128, 148 of the first and second control knobs 120, 140. For example, a substantially equal width of the gripping surface 148 of the second control knob 140 as compared to the width of the gripping surfaces 128 of the first control knob 120 may improve thumb/finger grip (e.g., reduced or minimize slipping due to wet gloves, etc.) across/along the entire rotation (e.g., outer circumference) of the crests and troughs of the first and second control knobs 120, 140. In addition, or alternatively, an increased width of the gripping surface 148 of the second control knob 140 may reduce or eliminate the uncomfortable "poking effect" often experienced by physicians when grasping/contacting thinner crest (s) of a conventional second control knob with a surface of their thumb or finger.

Figures 3A, 3B:
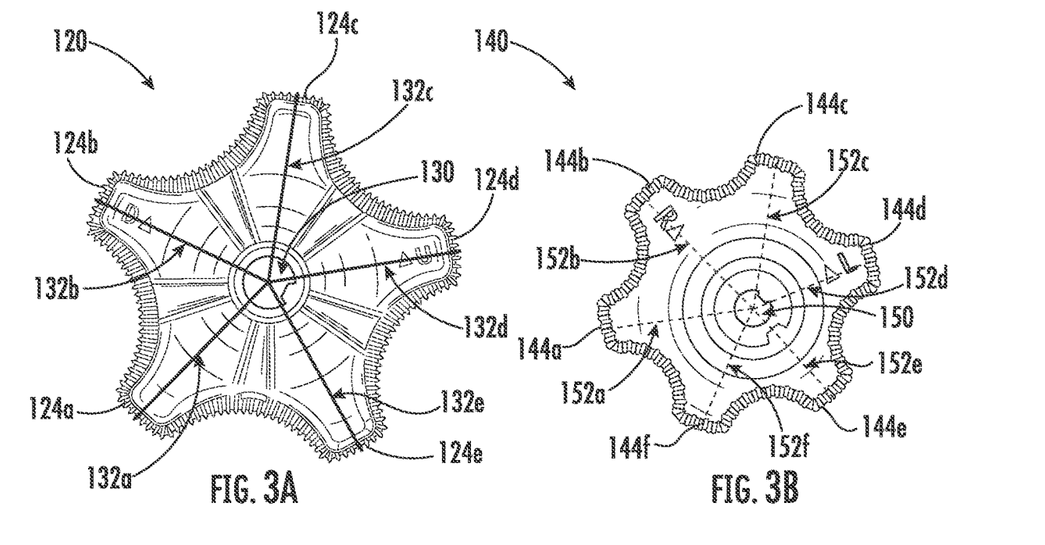
FIGS. 3A-3C provide perspective views of embodiments of first and second control knobs of an endoscope handle, according to the present disclosure.
Figure 3C:
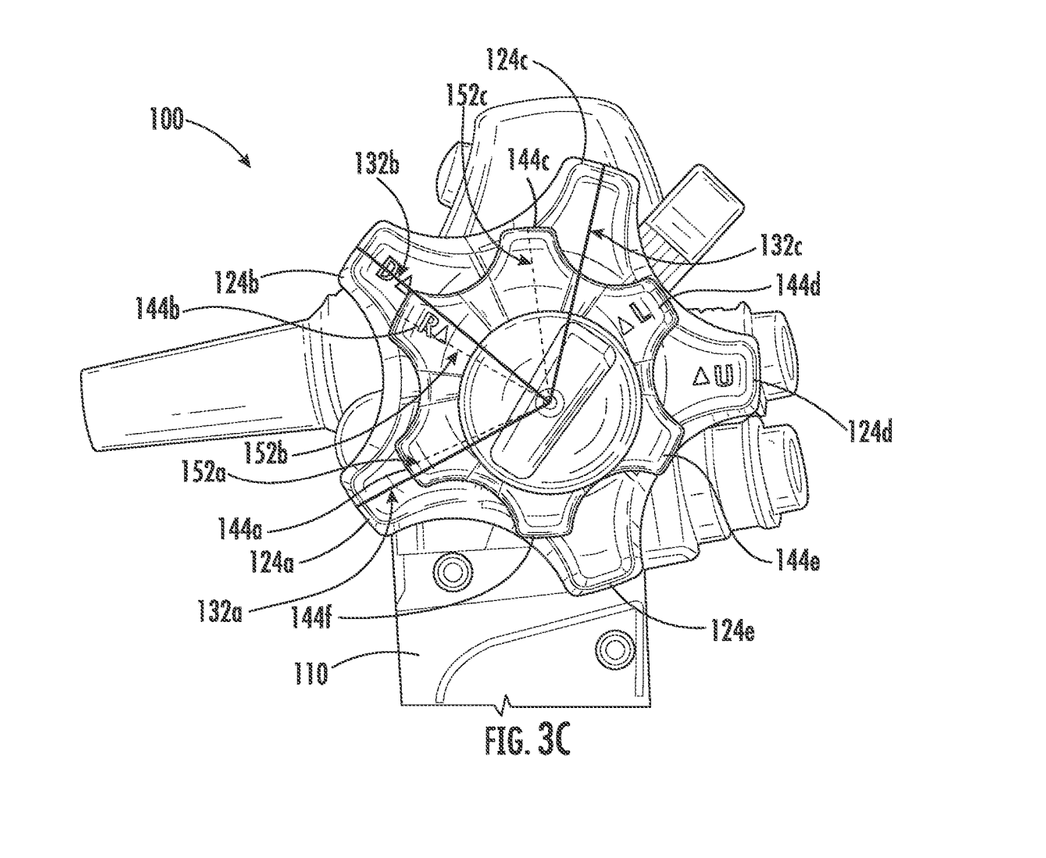

Referring to FIGS. 3A-3C, in one embodiment, the first control knob 120 may define a first opening 130 configured to receive a first portion 114 of a post 112 (e.g., mounting shaft; FIG. 1C) of the control handle 110, and the second control knob 140 may define a second opening 150 configured to receive a second portion 116 of the post 112 of the control handle 110. The first opening 130 may be substantially centered within (e.g., coaxial, geometrically centered, axis of rotation at a geometric center, etc.) the first control knob 120 such that a lever arm length (e.g., radius) 132*a-e* from the center of the first opening 130 to an end of each crest 124*a-e* is substantially equal. For example, the lever arm length 132*a-e* of each crest 124*a-e* of the first control knob 120 may be approximately 35.0 mm. In addition, the second opening 150 may be substantially off-center within (e.g., not geometrically centered within, axis of rotation not at a geometric center, etc.) the second control knob 140 such that a lever arm length 152*b* from the center of the first opening 150 to an end of a second crest 144*b* (e.g., crest B) of the series of crests 144*a-f* may be greater than a lever arm length from the center of the first opening 150 to an end of a first crest 144*a* (e.g., crest A) and an end of a third crest 144*c* (e.g., crest C) of the series of crests 144*a-f*. For example, the lever arm length 152*b* of the second crest 144*b* may be approximately 31.0 mm±2 mm and a lever arm length 152*a*, 152*c* of the first and third crests 144*a*, 144*c* may be approximately 29.0 mm±2 mm. In one embodiment, the second crest 144*b* may be disposed between the first and third crests 144*a*, 144*c*. In various additional embodiments, a lever arm length from the center of the first opening 150 to an end of a fourth crest 144*d* (e.g., crest D), fifth crest 144*e* (e.g., crest E) and sixth crest 144*f* (e.g., crest F) of the series of crests 144*a-f* may be less than the lever arm length of the first and third crests 144*a*, 144*c*.

Referring to the embodiment of FIG. 3A-3C, the torque generated on (e.g., applied to) a crest 124*a-e* of the first control knob 120 may be determined using the formula $T_B=F_B \times R_B$, where $T_B$ represents torque output, $F_B$ represents the force applied to a selected crest 124*a-e* of the first control knob 120 and $R_B$ represents the lever arm length 132*a-e* of the selected crest 124*a-e*. Similarly, the torque generated on (e.g., applied to) a crest 144*a-f* of the second control knob 140 may be determined using the formula $T_{S\_O}=F_{S\_O} \times R_{S\_O}$, where $T_{S\_O}$ represents torque output, $F_{S\_O}$ represents the force applied to a selected crest 144*a-f* of the second control knob 140 and $R_{S\_O}$ represents the lever arm length 152*a-f* of the selected crest 144*a-f*.

Referring to these formulas, with the lever arm lengths 132*a-e* of the respective crests 124*a-e* of the first control knob 120 being substantially equal, the torque output ($T_B$) required for the physician to rotate the first control knob 120 is substantially equal at each crest 124*a-e*. In comparison, with the second crest 144*b* of the second control knob 140 having a lever arm length 152*b* greater than a lever arm length 152*a*, 152*c* of the first and third crests 144*a*, 144*c* of the second control knob 140, the torque output ($T_{S\_O}$) required for the physician to rotate the second control knob 140 at the second crest 144*b* may be less than the torque output ($T_{S\_O}$) required for the physician to rotate the second control knob 140 at the first or third crests 144*a*, 144*c*. Similarly, the torque output ($T_{S\_O}$) required for the physician to rotate the second control knob 140 at the first or third crests 144*a*, 144*c* may be less than the torque output required for the physician to rotate the second control knob 140 at the fourth 144*d*, fifth 144*e*, and sixth 144*f* crests (e.g., which have lever arm lengths less than the lever arm lengths of the first, second and third crests 144*a-c*). As above, none of the crests 124*a-e* of the first control knob 120 may provide the physician with a mechanical advantage (e.g., reduced torque output $T_B$ to rotate the first control knob 120) as compared to another one of the crests 124*a-e*. In comparison, the torque output ($T_{S\_O}$) of the second crest 144*b* may provide the physician with a mechanical advantage (e.g., reduced torque output $T_S$ to rotate the second control knob 140) as compared to the torque output ($T_{S\_O}$) of the first and third crests 144*a*, 144*c*. In other words, the force required by the physician to rotate the second control knob 140 at the second crest 144*b* is less than the torque to rotate the second control knob 140 at the first and third crests 144*a*, 144*c* to achieve the same or similar torque output from the second control knob 140. Similarly, the torque output ($T_{S\_O}$) of the first and third crests 144*a*, 144*c* may provide the physician with a mechanical advantage (e.g., reduced torque output $T_S$ to rotate the second control knob 140) as compared to the torque output ($T_{S\_O}$) of the fourth 144*d*, fifth 144*e* and sixth 144*f* crests. It will also be appreciated that the reach to the first, second, and third crests 144*a*, 144*b*, 144*c* of the second control knob 140 of FIGS. 3A and 3B is generally improved when compared to the first, second, and third crests 144*a*, 144*b*, 144*c* of the second control knob 140 of FIGS. 2A and 2B. The maximum lever arm length available to rotate the knob (the distance from the crest to the axis of rotation) is the maximum radius of the knob at the top of the crest. Offsetting the center of rotation results in the knob moving towards the user and the lever arm length increasing. For the same applied force, the torque generated to rotate the distal tip of the endoscope increases as the lever arm length increases. Thus, the physician can apply less force to the control knob of FIGS. 3A and 3B to achieve the same amount of torque as achieved by the control knob of FIGS. 2A and 2B.

In use and by way of example, a physician may grasp a control handle 110 of an endoscope with their left hand and extend their left thumb to contact the first and second control knobs 120, 140. As described above, the physician may experience difficulty reaching the control knobs, especially the more distant second control knob 140 and especially if the physician has small hands. This difficulty may result in over-stretching of the left thumb and/or constant readjustment of the left hand/left thumb to alternately access the control knobs 120, 140. In various embodiments, the increased lever arm length of the second crest 144*b* (e.g., as compared to the first and third crests 144*a*, 144*c*) as well as the increased lever arm length of the first and third crests 144*a*, 144*c* (e.g., as compared to the fourth 144*d*, fifth 144*e* and sixth 144*f* crests), e.g., as may be achieved by moving the center of rotation of the second control knob 140 away from the geometric center, may provide the physician with an improved ability to reach, and reduced torqueing effort to rotate, the second control knob 140. It should be appreciated that while the torque output ($T_{S\_O}$) of the first and third crests 144a, 144c may be greater than the torque output ($T_{S\_O}$) of the second crest 144b, the torque output ($T_{S\_O}$) of the first and third crests 144a, 144c may be less than the torque output ($T_S$) of the corresponding first and third crests of FIGS. 2A-2C (e.g., in which the second opening 150 is substantially centered within the second control knob 140).

Figure 4A:
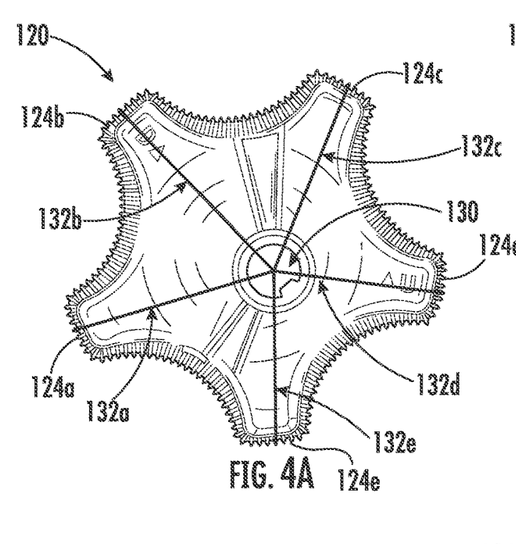
FIGS. 4A-4C provide perspective views of embodiments of first and second control knobs of an endoscope handle, according to the present disclosure.
Figure 4B:
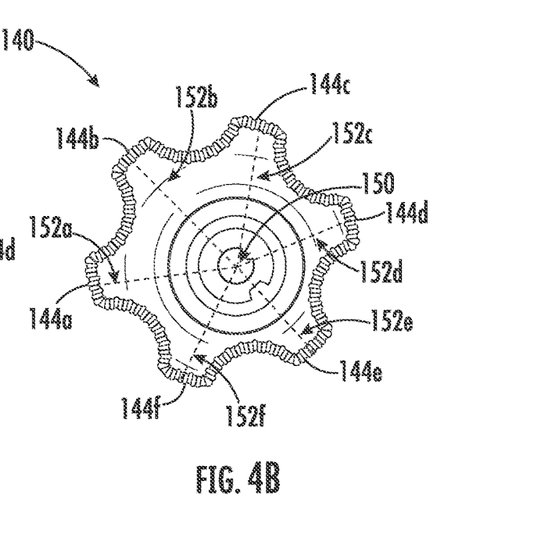
Figure 4C:
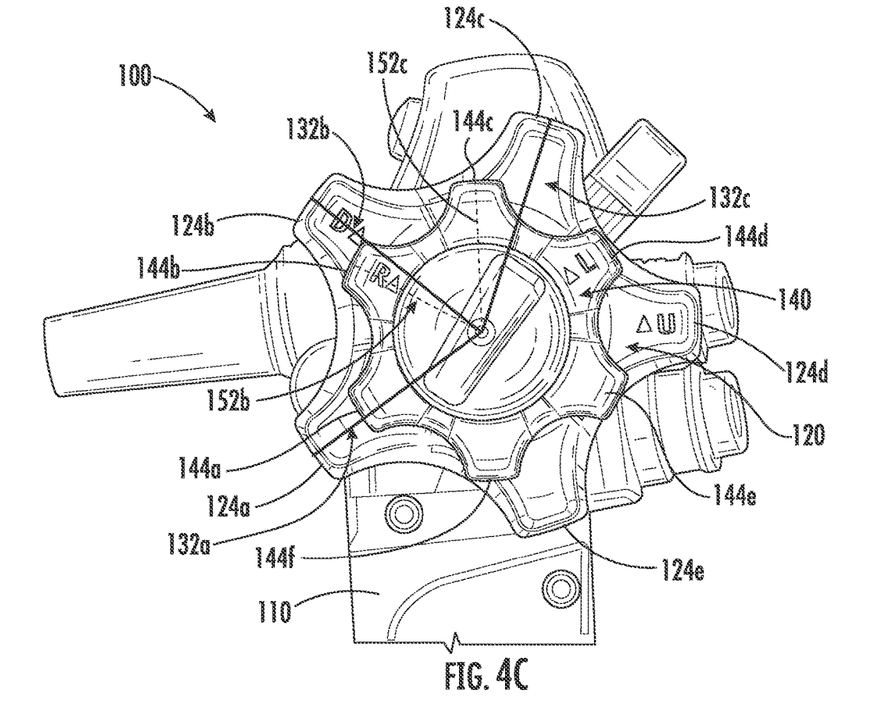

Referring to FIGS. 4A-4C, in one embodiment, the first control knob 120 may define a first opening 130 configured to receive a first portion 114 of a post 112 (e.g., mounting shaft; FIG. 1C) of the control handle 110, and the second control knob 140 may define a second opening 150 configured to receive a second portion 116 of the post 112 of the control handle 110. The first opening 130 may be substantially off-center within (e.g., not geometrically centered within, axis of rotation not at a geometric center, etc.) the first control knob 120 such that a lever arm length (e.g., radius) 132b from the center of the first opening 130 to an end of a second crest 124b (e.g., crest B) of the series of crests 124a-e may be greater than a lever arm length 132a, 132c from the center of the first opening 130 to an end of a first crest 124a (e.g., crest A) and an end of a third crest 124c (e.g., crest C) of the series of crests 124a-e. For example, the lever arm length 132b of the second crest 124b may be approximately 39.0 mm and a lever arm length 132a, 132c of the first and third crests 124a, 124c may be approximately 36.0 mm. In one embodiment, the second crest 124b may be disposed between the first and third crests 124a, 124c. In various additional embodiments, a lever arm length from the center of the first opening 150 to an end of a fourth crest 124d (e.g., crest D) and fifth crest 124e (e.g., crest E) of the series of crests 124a-e may be less than the lever arm length of the first and third crests 124a, 124c. In addition, the second opening 150 may be substantially off-center within (e.g., not geometrically centered, axis of rotation not at a geometric center, etc.) the second control knob 140 such that a lever arm length 152b from the center of the first opening 150 to an end of a second crest 144b (e.g., crest B) of the series of crests 144a-f may be greater than a lever arm length 152a, 152c from the center of the first opening 150 to an end of a first crest 144a (e.g., crest A) and an end of a third crest 144c (e.g., crest C) of the series of crests 144a-f. For example, the lever arm length 152b of the second crest 144b may be approximately 31.0 mm and a lever arm length 152a, 152c of the first and third crests 144a, 144c may be approximately 29.0 mm. In one embodiment, the second crest 144b may be disposed between the first and third crests 144a, 144c. In various additional embodiments, a lever arm length from the center of the first opening 150 to an end of a fourth crest 144d (e.g., crest D), fifth crest 144e (e.g., crest E) and sixth crest 144f (e.g., crest F) of the series of crests 144a-f may be less than the lever arm length of the first and third crests 144a, 144c.

Referring to the embodiment of FIG. 4A-4C, the torque generated on (e.g., applied to) a crest 124a-e of the first control knob 120 may be determined using the formula $T_{B\_O}=F_{B\_O} \times R_{B\_O}$, where $T_{B\_O}$ represents torque output, $F_{B\_O}$ represents the force applied to a selected crest 124a-e of the first control knob 120 and $R_{B\_O}$ represents the lever arm length 132a-e of the selected crest 124a-e. Similarly, the torque generated on (e.g., applied to) a crest 144a-f of the second control knob 140 may be determined using the formula $T_{S\_O}=F_{S\_O} \times R_{S\_O}$, where $T_{S\_O}$ represents torque output, $F_{S\_O}$ represents the force applied to a selected crest 144a-f of the second control knob 140 and $R_{S\_O}$ represents the lever arm length 152a-f of the selected crest 144a-f.

Referring to these formulas, with the second crest 124b having a lever arm length 132b greater than a lever arm length 132a, 132c of the first and third crests 124a, 124c, the torque output ($T_{B\_O}$) required for a physician to rotate the first control knob 120 at the second crest 124b may be less than the torque output ($T_{B\_O}$) required for the physician to rotate the first control knob 120 at the first or third crests 124a, 124c. Similarly, the torque output ($T_{B\_O}$) required for the physician to rotate the first control knob 120 at the first or third crests 124a, 124c may be less than the torque output required for the physician to rotate the first control knob 120 at the fourth 124d and fifth 124e crests. In addition, with the second crest 144b having a lever arm length 152b greater than a lever arm length 152a, 152c of the first and third crests 144a, 144c, the torque output ($T_{S\_O}$) required for the physician to rotate the second control knob 140 at the second crest 144b may be less than the torque output ($T_{S\_O}$) required for the physician to rotate the second control knob 140 at the first or third crests 144a, 144c. Similarly, the torque output ($T_{S\_O}$) required for the physician to rotate the second control knob 140 at the first or third crests 144a, 144c may be less than the torque output required for the physician to rotate the second control knob 140 at the fourth 144d, fifth 144e and sixth 144f crests. The torque output ($T_{B\_O}$) of the second crest 124b may therefore provide the physician with a mechanical advantage (e.g., reduced torque output $T_{B\_O}$ to rotate the second control knob 140) as compared to the torque output ($T_{B\_O}$) of the first and third crests 124a, 124c. Similarly, the torque output ($T_{B\_O}$) of the first and third crests 124a, 142c may provide the physician with a mechanical advantage (e.g., reduced torque output $T_{B\_O}$ to rotate the second control knob 140) as compared to the torque output ($T_{B\_O}$) of the fourth 124d and fifth 124e crests (e.g., which have lever arm lengths less than the lever arm lengths of the first, second and third crests 124a-c). Similarly, the torque output ($T_{S\_O}$) of the second crest 144b may provide the physician with a mechanical advantage (e.g., reduced torque output $T_{S\_O}$ to rotate the second control knob 140) as compared to the torque output ($T_{S\_O}$) of the first and third crests 144a, 144c. Similarly, the torque output ($T_{S\_O}$) of the first and third crests 144a, 144c may provide the physician with a mechanical advantage (e.g., reduced torque output $T_S$ to rotate the second control knob 140) as compared to the torque output ($T_{S\_O}$) of the fourth 144d, fifth 144e and sixth 144f crests (e.g., which have lever arm lengths less than the lever arm lengths of the first, second and third crests 144a-c).

In use and by way of example, a physician may grasp a control handle 110 of an endoscope with their left hand and extend their left thumb to contact the first and second control knobs 120, 140. In various embodiments, the increased lever arm length 132b of the second crest 124b (e.g., as compared to the first and third crests 124a, 124c) as well as the increased lever arm length 132a, 132c of the first and third crests 124a, 124c (e.g., as compared to the fourth 124d and fifth 124e crests), e.g., as may be achieved by moving the center of rotation of the first control knob 120 off-center (e.g., away from geometric center), may provide the physician with an improved ability to reach, and reduced torqueing effort to rotate, the first control knob 120. In various additional embodiments, the increased lever arm length 152b of the second crest 144b (e.g., as compared to the first and third crests 144a, 144c) as well as the increased lever arm length 152a, 152c of the first and third crests 144a, 144c (e.g., as compared to the fourth 144d, fifth 144e and sixth 144f crests), e.g., as may be achieved by moving the center of rotation of the second control knob 140 off-axis (e.g., away from the geometric center), may provide the physician with an improved ability to reach, and reduced torqueing effort to rotate, the second control knob 140. It should be appreciated that while the torque output ($T_{B\_O}$) of the first and third crests 124a, 124c may be greater than the torque output ($T_{B\_O}$) of the second crest 124b, the torque output ($T_{B\_O}$) of the first and third crests 124a, 124c may be less than the torque output ($T_B$, $T_{B\_O}$) of the corresponding first and third crests of FIGS. 2A-2C and/or FIGS. 3A-3C (e.g., in which the second opening 150 is substantially centered within the second control knob 140). It should also be appreciated that while the torque output ($T_{S\_O}$) of the first and third crests 144a, 144c may be greater than the torque output ($T_{S\_O}$) of the second crest 144b, the torque output ($T_{S\_O}$) of the first and third crests 144a, 144c may be less than the torque output ($T_S$) of the corresponding first and third crests of FIGS. 2A-2C (e.g., in which the second opening 150 is substantially centered within the second control knob 140).

Figure 5A:
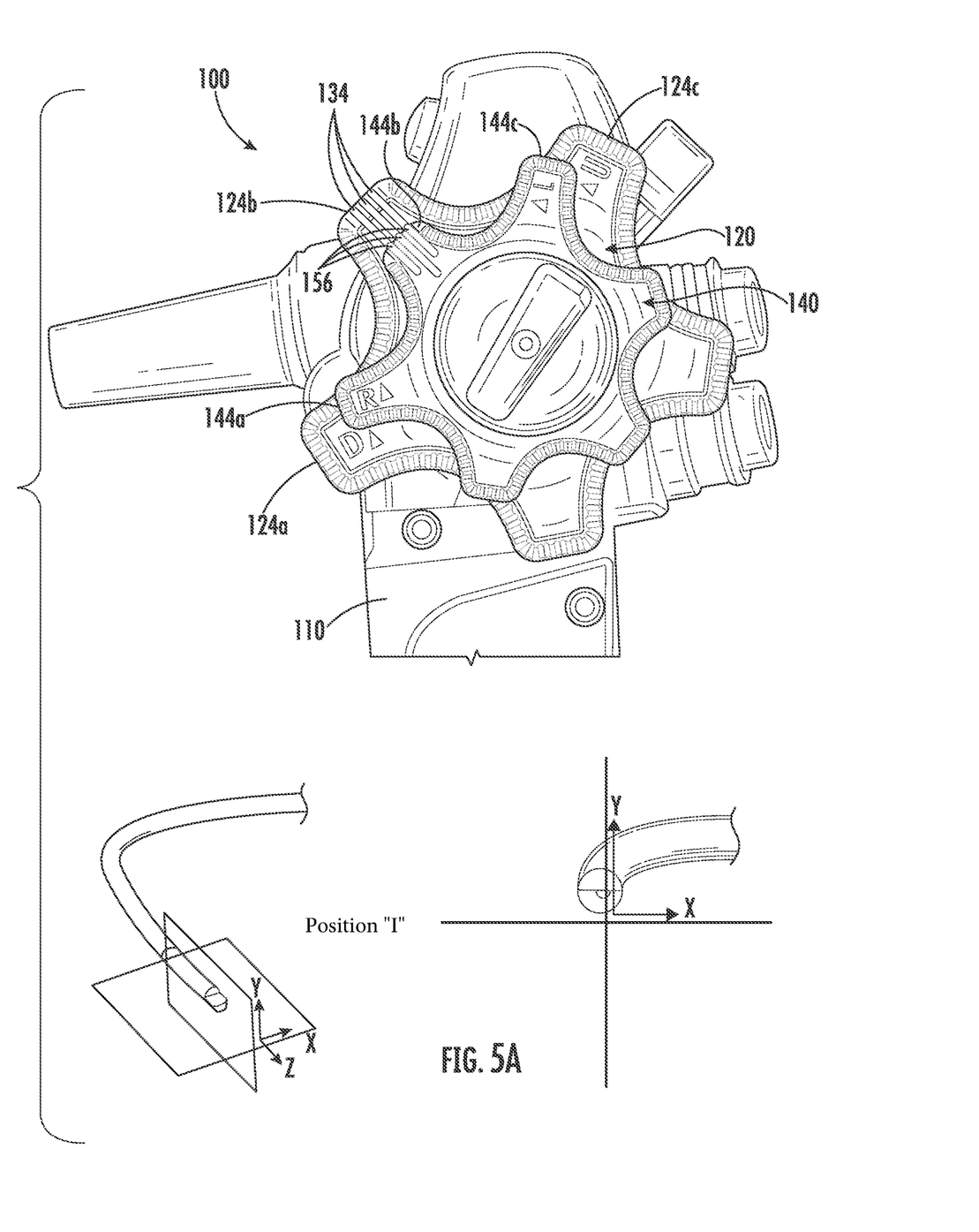
FIGS. 5A-5D provide perspective views of embodiments of first and second control knobs of an endoscope handle, according to one embodiment of the present disclosure.

Referring to FIG. 5A, in one embodiment, the first control knob 120 may define a first opening 130 configured to receive a first portion 114 of a post 112 (e.g., mounting shaft; FIG. 1C) of the control handle 110, and the second control knob 140 may define a second opening 150 configured to receive a second portion 116 of the post 112 of the control handle 110. The first and second openings 130, 150 may be substantially centered within (e.g., coaxial, geometrically centered, axis of rotation at a geometric center, etc.) the first and second control knobs 120, 140. In one embodiment, a lever arm length 132a, 132c from the center of the first opening 130 to an end of a first crest 124a (e.g., crest A) and an end of a third crest 124c (e.g., crest C) of the series of crests 124a-e may be greater than a lever arm length 132b from the center of the first opening 130 to an end of a second crest 124b (e.g., crest B) of the series of crests 124a-e. For example, the lever arm length 132b of the second crest 124b may be approximately 35.0 mm and a lever arm length 132a, 132c of the first and third crests 124a, 124c may be approximately 38.0 mm. In one embodiment, a lever arm length 152a, 152c from the center of the first opening 150 to an end of a first crest 144a (e.g., crest A) and an end of a third crest 144c (e.g., crest C) of the series of crests 144a-f may be greater than a lever arm length 152b from the center of the first opening 150 to an end of a second crest 144b (e.g., crest B) of the series of crests 144a-f. For example, the lever arm length 152b of the second crest 144b may be approximately 27.0 mm and a lever arm length of the first and third crests 144a, 144c may be approximately 32.0 mm. In another example, the lever arm length 152b of the second crest 144b may be approximately 32.0 mm and a lever arm length of the first and third crests 144a, 144c may be approximately 27.0 mm.

Referring to the embodiment of FIG. 5A, the torque generated on (e.g., applied to) a crest 124a-e of the first control knob 120 may be determined using the formula $T_{E\_B}=F_{E\_B} \times R_{E\_B}$, where $T_{E\_B}$ represents torque output, $F_{E\_B}$ represents the force applied to a selected crest 124a-e of the first control knob 120 and $R_{E\_B}$ represents the lever arm length 132a-e of the selected crest 124a-e. Similarly, the torque generated on (e.g., applied to) a crest 144a-f of the second control knob 140 may be determined using the formula $T_{E\_S}=F_{E\_S} \times R_{E\_S}$, where $T_{E\_S}$ represents torque output, $F_{E\_S}$ represents the force applied to a selected crest 144a-f of the second control knob 140 and $R_{E\_S}$ represents the lever arm length 132a-e of the selected crest 144a-f.

Referring to these formulas, with the first and third crests 124a, 124c having a lever arm length 132a, 132c greater than a lever arm length 132b of the second crest 124b, the torque output ($T_{E\_B}$) required for the physician to rotate the first control knob 120 at the first or third crest 124a, 124c may be less than the torque output ($T_{E\_B}$) required for the physician to rotate the first control knob 120 at the second crest 124b. In other words, the force required by the physician to rotate the second control knob 140 at the first and third crests 144a, 144c is less than the torque to rotate the second control knob 140 at the second crest 144b to achieve the same or similar torque output from the second control knob 140. In addition, with the first and third crests 144a, 144c having a lever arm length 152a, 152c greater than a lever arm length 152b of the second crest 144b, the torque output ($T_{E\_S}$) required for the physician to rotate the second control knob 140 at the first and third crests 144a, 144c may be less than the torque output ($T_{E\_S}$) required for the physician to rotate the second control knob 140 at the second crest 144b. The first and third crests 124a, 124c of the first control knob 120 may therefore provide the physician with a mechanical advantage (e.g., reduced torque output $T_{E\_S}$ to rotate the first control knob 120) as compared to the torque output of crests 124b, 124d and/or 124e. Similarly, the torque output ($T_{E\_S}$) of the first and third crests 144a, 144c may provide the physician with a mechanical advantage (e.g., reduced torque output $T_{E\_S}$ to rotate the second control knob 140) as compared to the torque output of crests 144b and/or 144d-f.

In use and by way of example, a physician may grasp a control handle 110 of an endoscope with their left hand and extend their left thumb to contact the first and second control knobs 120, 140. In various embodiments, the increased lever arm length of the first and third crest 124a, 124c (e.g., as compared to the second crests 124b), achieved by extending the length of the first and third crests 124a, 124c, may provide the physician with an improved ability to reach, and reduced torqueing effort to rotate, the first control knob 120 when engaging the first or third crests 124a, 124c. In various additional embodiments, the increased lever arm length of the first and third crests 144a, 144c (e.g., as compared to the second crest 144b) achieved by extending the length of the first and third crests 144a, 144c may provide the physician with an improved ability to reach, and reduced torqueing effort to rotate, the second control knob 140 when engaging the first or third crests 144a, 144c. In various embodiments, the lever arm lengths of crests 124a, 124c, 144a, 144c may provide the physician with the maximum mechanical advantage when the distal tip of the endoscope is bent or angled at or near its maximum functional limit and therefore require the maximum amount of force/torque to move the distal tip (e.g., up/down and left/right).

In one embodiment, an outer surface of the first crests 124a, 144a and an outer surface of the third crests 124c, 144c of the respective first and second control knobs 120, 140 may be substantially smooth or otherwise different from an outer surface of the second crests 124b, 144b of the respective first and second control knobs 120, 140, which may include an integrated surface feature 134, 154 (e.g., dimples, raised lines, projections, etc.) to provide tactile feel/feedback to the physician. Conversely, an outer surface of the first crests 124a, 144a and an outer surface of the third crests 124c, 144c of the respective first and second control knobs 120, 140 may include an integrated surface feature, while the outer surface of the second crests 124b, 144b of the respective first and second control knobs 120, 140 may be smooth or otherwise different. It will be appreciated that any or all of the crests 124a-e, 144a-f may include an integrated surface feature 134, 154 to provide tactile feel/feedback to the physician.

As will be understood by those of skill in the art, the position of a patient on an operating table may vary (e.g., prone, semi-prone, supine, etc.) depending on the physician's preference, the layout of the surgical suite and/or the medical procedure being performed. These varied patient positions often result in the endoscope being advanced to a target location along a complex three-dimensional path. Physicians typically advance/manipulate the endoscope within the patient by relying on a three-dimensional video image provided by a camera located at the distal end of the endoscope and a two-dimensional fluoroscopic image. The two-dimensional fluoroscopic image often makes it difficult for the physician to track and/or determine the three-dimensional orientation of the distal end of the endoscope and/or the portion of the endoscope shaft extending behind the camera, thereby leading to potential confusion between up/down movement (e.g., using the first control knob) and left/right movement (e.g., using the second control knob).

Figure 5B:
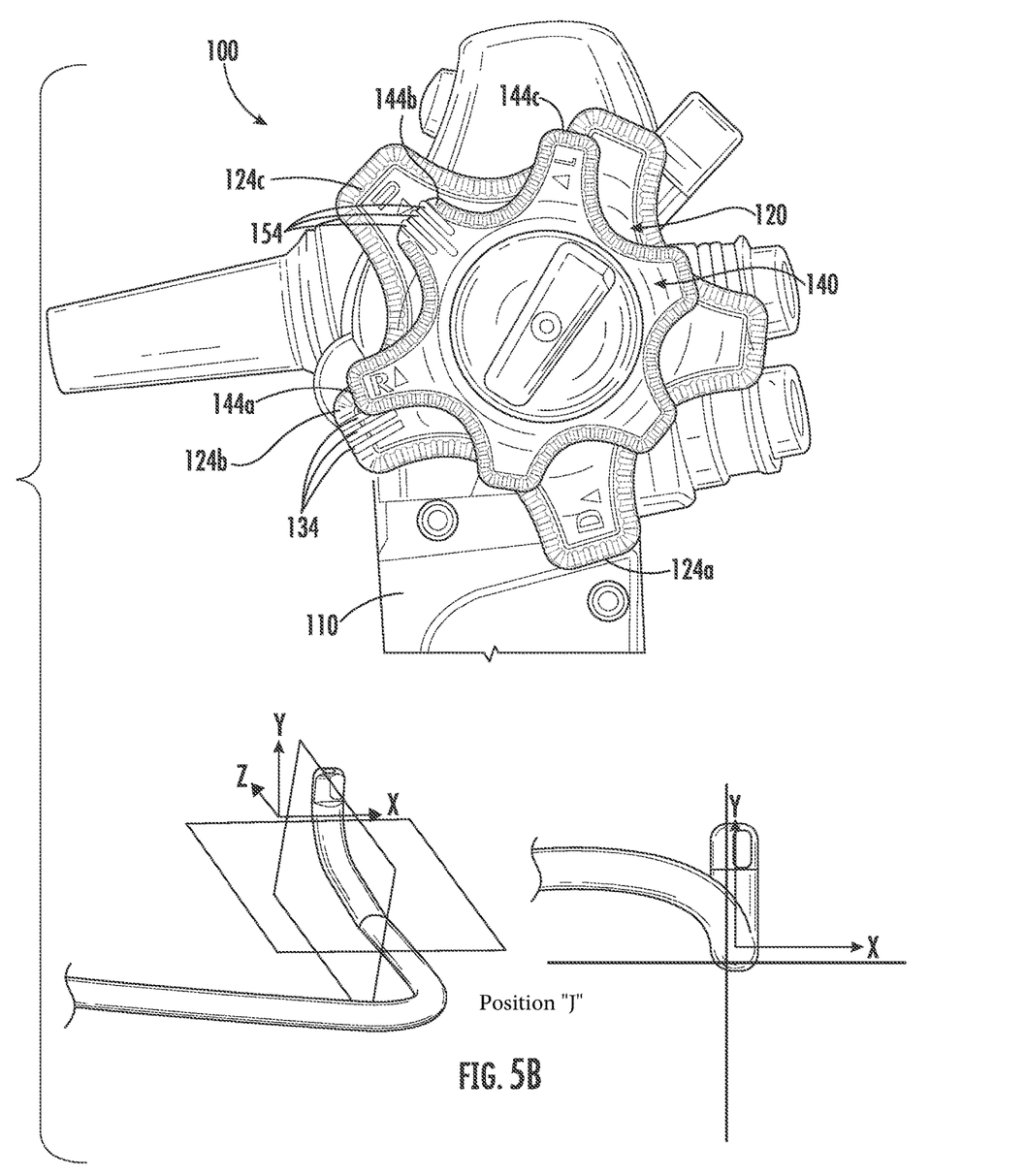
Figure 5C:
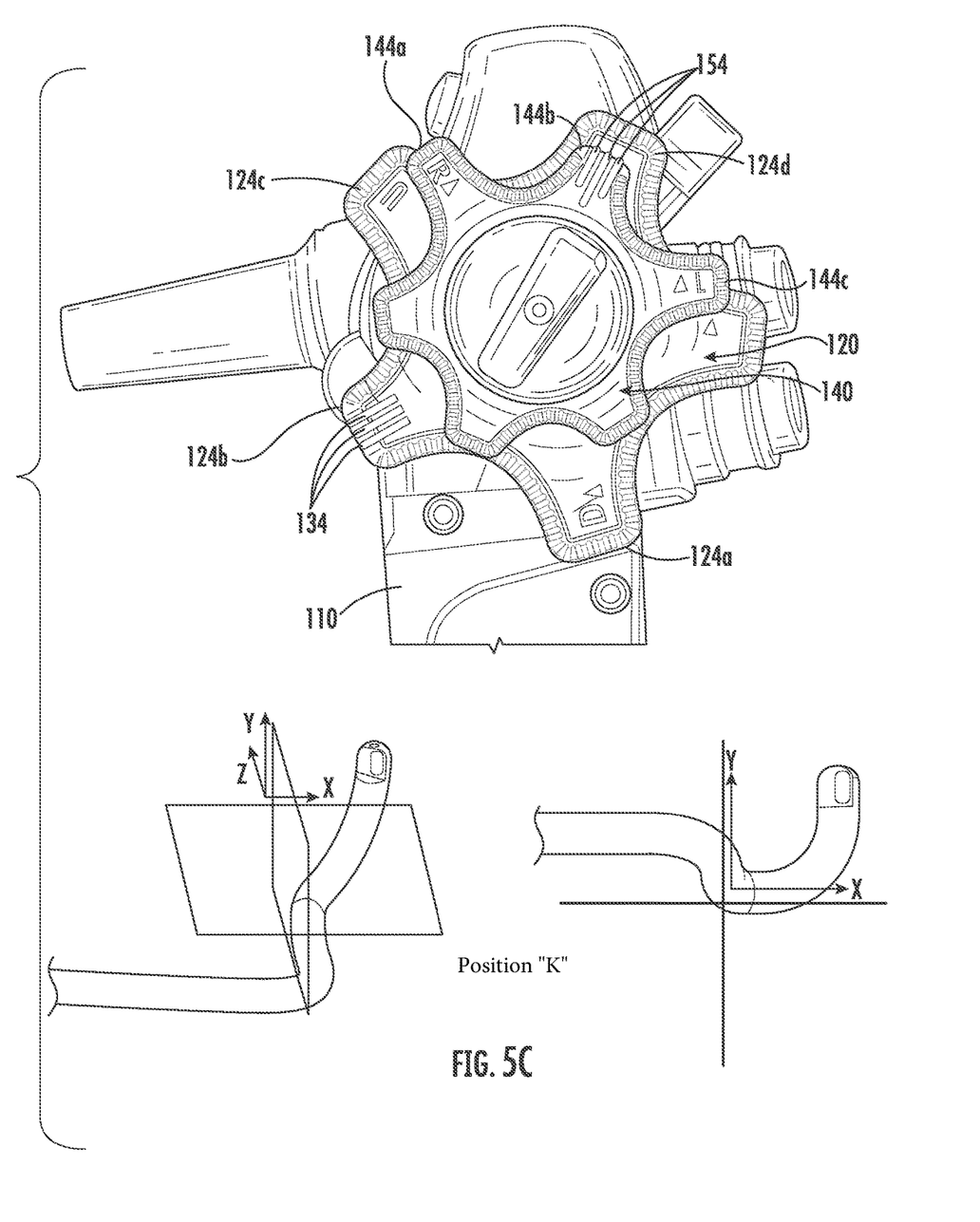
Figure 5D:
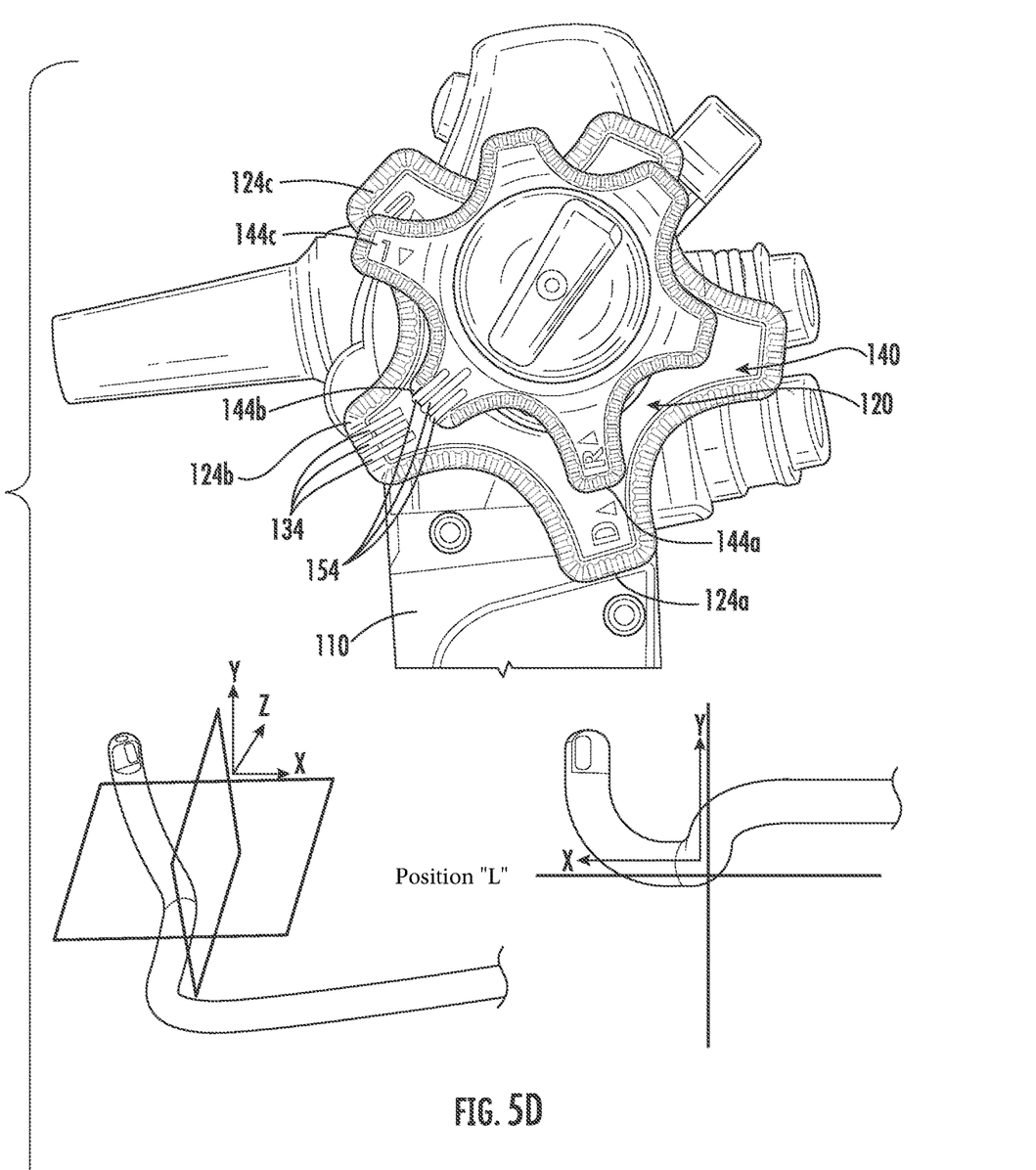

In various embodiments, the tactile feel provided by the integrated surface features 134, 154 on the second crests 124b, 144b of the first and second control knobs 120, 140 may allow the physician to determine/identify the relative location of the first and second crests 124b, 144b, and therefore the three-dimensional orientation of the distal end and/or distal portion of the endoscope, without looking directly at the control handle 110 and away from the video monitor and/or fluoroscopic image. As outlined below, the physician may then rotate the first and/or second control knobs 120, 140 to precisely manipulate the distal end/distal portion of the endoscope in three-dimensions. For example, referring to FIG. 5A, with the second crests 124b, 144b of the first and second control knobs 120, 140 aligned (e.g., in the neutral position; knob position "I") the distal tip of the endoscope is in a straight configuration, with the profile of the endoscope shaft in a single plane and without any substantial strain or torque. Referring to FIG. 5B, with the first and second control knobs in the "I" position, the first control knob 120 may be rotated down (e.g., counterclockwise) such that the second crest 124b of the first control knob is aligned with the first crest 144a of the second control knob 140 (e.g., knob position "J"). With the first and second control knobs in the "J" position, the distal end of the endoscope may move up and with the profile of the endoscope shaft in a single plane. Referring to FIG. 5C, with the first and second control knobs in the "J" position, the second control knob 140 may then be rotated up (e.g., clockwise) such that the second crest 144b of the first control knob is aligned with the fourth crest 124d of the second control knob 140 (e.g., knob position "K"). With the first and second control knobs in the "K" position the distal end of the endoscope may move to the right. Referring to FIG. 5D, with the first and second control knobs in the "K" position, the second control knob 140 may then be rotated down (e.g., counterclockwise; knob position "L") such that the first crest 124a of the first control knob 120 is aligned with the first crest 144a of the second control knob 140. With the first and second control knobs returned to the "L" position the distal end of the endoscope may move up and to the left.

In various embodiments, the first and second control knobs 120, 140 of the various embodiments depicted in FIGS. 1A-5D may provide a variety of advantages as compared to conventional endoscope handle control knobs. For example, the first and second control knobs may provide improved ergonomics and ease-of-use for a physician to rotate and/or maintain the position of the distal end of an endoscope within a patient. Improved control of distal tip movement of the endoscope may also decrease medical procedure times and/or increase efficiency, with beneficial results realized by both the patient (e.g., improved procedure outcome) and the physician (e.g., shorter procedure times leading to reduced fatigue, etc.). In addition, because different types of endoscopes (e.g., duodenoscopes, EUS scopes, colonoscopes, etc.) typically include the same knob interfaces (e.g., mounting shafts), the first and/or second control knobs 120, 140 disclosed herein may be readily incorporated onto any endoscope handle. The ability of the control knobs to be used interchangeably (e.g., in various combinations of the embodiments outlined above), may provide improved adaptability among physicians with different hand sizes and/or operating preferences.

In various embodiments, any or all of the components of the control knobs 120, 140 disclosed herein may be formed from (e.g., injection molded, co-extruded) or otherwise include a variety of rigid thermoplastic polymers that are resistant to various disinfecting or sterilizing modalities (e.g., chemicals, radiation, U.V. light), including, for example, polycarbonate, ABS, nylon, glass-reinforced nylon, acetal acrylic, PEET, PEEK, Pebax, polypropylene and the like.

In various embodiments, the lever arm length(s) of any crest(s) of the first or second control knobs are exemplary and can be varied in relation to each other to optimize ergonomics for a particular desired application. In addition, or alternatively, force may be applied to any side, edge or surface of any of the troughs and/or crests of the first and second control knobs from any direction (e.g., pushing with the thumb on top of a crest, pushing with a finger on a slope of the crest, etc.)

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
   a control handle operably attached to a proximal end of a shaft;
   a first control knob rotatably attached to the control handle via a first opening of the first control knob and configured to move a distal end of the shaft in a first direction; and
   a second control knob rotatably attached to the control handle via a second opening of the second control knob,
   wherein the first opening is geometrically centered within the first control knob;
   wherein the second opening is geometrically off-center within the second control knob; and
   wherein an outer circumference of the first control knob is defined by a plurality of radially outermost points, wherein a first lever arm length extending from the first opening to an end of a first radially outermost point is greater than a second lever arm length extending from the first opening to an end of a second radially outermost point of the plurality of radially outermost points, and wherein a first texture of the first radially outermost point is different from a second texture of the second radially outermost point.

2. The medical device of claim 1, wherein the outer circumference of the first control knob includes a gripping surface.

3. The medical device of claim 2, wherein:
the outer circumference of the first control knob is further defined by a plurality of valleys,
each of the plurality of valleys is located between adjacent radially outermost points of the plurality of radially outermost points, and
the gripping surface extends an entirety of the outer circumference of the first control knob.

4. The medical device of claim 2, wherein the gripping surface includes the first texture and the second texture.

5. The medical device of claim 2, wherein the first control knob is comprised of a first material, and the gripping surface is comprised of a second material different than the first material.

6. The medical device of claim 1, wherein an exterior surface having at least one of the plurality of radially outermost points includes an integrated surface feature to provide tactile feedback for identifying a position of the first control knob and an associated orientation of the distal end of the shaft.

7. A medical device, comprising:
a control handle operably attached to a proximal end of a shaft;
a first control knob rotatably attached to the control handle via a first opening of the first control knob and configured to move a distal end of the shaft in a first direction;
wherein the first opening is geometrically centered within the first control knob;
wherein an outer circumference of the first control knob is defined by a first plurality of radially outermost points; and
a second control knob rotatably attached to the control handle via a second opening of the second control knob and configured to move a distal end of the shaft in a second direction;
wherein the second opening is geometrically off-centered within the second control knob;
wherein an outer circumference of the second control knob is defined by a second plurality of radially outermost points each including a lever arm length from a center of the second opening to the respective radially outermost point from the second plurality of radially outermost points, and at least three lever arm lengths of the second plurality of radially outermost points are different from one another.

8. The medical device of claim 7, wherein each of the first plurality of radially outermost points includes a lever arm length from a center of the first opening to the respective radially outermost point from the first plurality of radially outermost points, and at least two lever arm lengths of the first plurality of radially outermost points are different from one another.

9. The medical device of claim 7, wherein the outer circumference of the first control knob includes a gripping surface of a same width as a gripping surface of the second control knob.

10. The medical device of claim 9, wherein:
the outer circumference of each of the first control knob and the second control knob is further defined by a plurality of valleys,
each of the plurality of valleys is located between adjacent radially outermost points of the respective first plurality of radially outermost points and the second plurality of radially outermost points, and
the gripping surface extends an entirety of the outer circumference of first control knob and the second control knob.

11. The medical device of claim 7, wherein each of an exterior surface having at least one of the first plurality of radially outermost points and an exterior surface having at least one of the second plurality of radially outermost points includes an integrated surface feature to provide tactile feedback for identifying a relative position of the first control knob and the second control knob and an associated orientation of the distal end of the shaft.

12. The medical device of claim 11, wherein each of the first and the second plurality of radially outermost points includes a first, a second, a third, a fourth, and a fifth radially outermost point, and the exterior surfaces that include the second radially outermost point of the first control knob and the second radially outermost point of the second control knob have the integrated surface feature.

13. The medical device of claim 12, wherein, when each of the first control knob and the second control knob is in a neutral position, the second radially outermost point of the first control knob and the second control knob are aligned, and the distal end of the shaft is in a straight configuration.

14. The medical device of claim 13, wherein the first direction includes up and down, and when the first control knob is rotated from the neutral position to a first position, the second radially outermost point of the first control knob is aligned with the first radially outermost point of the second control knob in the neutral position, and the distal end of the shaft moves up in the first direction.

15. The medical device of claim 13, wherein the second direction includes left and right, and when the second control knob is rotated from the neutral position to a first position, the second radially outermost point of the second control knob is aligned with the third radially outermost point of the first control knob in the neutral position, and the distal end of the shaft moves right.

16. The medical device of claim 15, wherein when the second control knob is rotated from the neutral position or the first position to a second position, the second radially outermost point of the second control knob is aligned with the first radially outermost point of the first control knob in the neutral position, and the distal end of the shaft moves left.

17. The medical device of claim 7, wherein the first control knob is disposed between the control handle and the second control knob.

18. The medical device of claim 7, wherein the second control knob is disposed between the control handle and the first control knob.

19. The medical device of claim 1, wherein the first lever arm length is approximately 38.0 mm, and the second lever arm length is approximately 35.0 mm.

* * * * *